United States Patent [19]

Takagi et al.

[11] Patent Number: 4,879,230

[45] Date of Patent: Nov. 7, 1989

[54] ESCHERICHIA COLI CANDIDA MALTOSA SACCHAROMYCES CEREVISIAE SHUTTLE VECTORS AND METHOD FOR MAKING

[75] Inventors: Masamichi Takagi, Fuchu; Keiji Yano, Tokyo; Ichiro Shibuya; Minoru Morikawa, both of Kashiwa, all of Japan

[73] Assignee: Nikka Whisky Distilling Co., Ltd., Tokyo, Japan

[21] Appl. No.: 813,193

[22] Filed: Dec. 24, 1985

[30] Foreign Application Priority Data

Sep. 27, 1985 [JP] Japan .................. 60-212187
Sep. 27, 1985 [JP] Japan .................. 60-212188

[51] Int. Cl.$^4$ .................. C12N 15/00; C12N 5/00; C12P 19/34
[52] U.S. Cl. .................. 435/172.3; 435/320; 435/91; 435/255; 435/256; 435/252.33; 536/27; 935/28; 935/37; 935/56; 935/69; 935/73
[58] Field of Search ............... 435/68, 91, 172.3, 255, 435/253, 320, 254; 935/28, 37

[56] References Cited

PUBLICATIONS

Takagi et al., *J. Bact.*, vol. 167(2) pp. 551–555, Aug. 1986, "Construction of a Host–Vector System in *Candida maltosa* by Using an ARS Site Isolated from Its Genome".

Gillum et al., *Mol Gen Genet*, vol. 198, pp. 179–182, 1984, "Isolation of the *Candida albicans* Gene for orotidine-5'-phosphate decarboxylse by complementation of *S. cerevisiae* ura3 and *E coli* pyrF Mutations".

Broach et al., *Gene.* vol. 8, pp. 121–133, 1979.

Ho et al., *Chem. Abst.*, vol. 103(5) No. 32483j, 1984, "Development of a Cloning System for Candida Species".

Kawamura et al., *Gene*, vol. 24, pp. 157–162, 1983, "Cloning of a Leu Gene and an ARS Site of *Candida maltosa*".

Rosenbluh et al., *Mol Gen Genet*, vol. 200, pp. 500–502, 1985, "Isolation of genes from *Candida albicans* by complementation in *Saccharomyces cerevisiae*".

Hsu et al., *J. Bact.*, vol. 154(3) Jun. 1983, pp. 1033–1039, "Construction of a New Yeast Cloning Vector Containing Autonomous Replication Sequences from *Candida utilis*".

*Primary Examiner*—Robin Teskin
*Attorney, Agent, or Firm*—Armstrong, Nikaido, Marmelstein, Kubovcik & Murray

[57] ABSTRACT

The present invention relates to plasmids whose hosts can be *Escherichia coli* and some kinds of yeasts, namely, shuttle vectors, as well as to processes for producing said plasmids. There are provided in the present invention (1) plasmids containing an autonomously replicating sequence of *Candida maltosa*, Leu 2 gene derived from *Saccharomyces cerevisiae* and an ampicillin resistance gene and (2) plasmids further containing a tetracycline resistance gene as well as the genes described in (1).

The plasmids (shuttle vectors) of the present invention can be utilized as follows. A useful foreign gene is inserted into plasmids of the present invention; using the resulting new plasid, *Escherichia coli* is transformed and cultured in order to obtain the plasmid in a large amount; and using this plasmid, *Saccharomyces cerevisiae* or *Candida maltosa* as a host is allowed to produce useful substances such as hormones and enzymes on a large scale.

4 Claims, 4 Drawing Sheets

E : EcoRI CLEAVAGE SITE
P : PstI CLEAVAGE SITE
H : HindIII CLEAVAGE SITE
B : BamHI CLEAVAGE SITE
S : SalI CLEAVAGE SITE B: BamHI CLEAVAGE SITE
H: HindIII CLEAVAGE SITE

ESCHERICHIA COLI CANDIDA MALTOSA SACCHAROMYCES CEREVISIAE SHUTTLE VECTORS AND METHOD FOR MAKING

BACKGROUND OF THE INVENTION

The present invention relates to plasmids whose hosts can be *Escherichia coli* and some kinds of yeasts, namely, shuttle vectors.

In recent years, attention is being paid to production of useful substances using a recombinant DNA technique brought about by the development of molecular biology and genetic engineering. As a method of producing useful substances or as a method of incorporating a useful gene into a microorganism, insertion of a gene of interest into a plasmid and subsequent transformation of a host microorganism are ordinarily conducted. In this case, in order to supplement the low frequency of transformation of yeast and to isolate a plasmid of interest in a large amount, required is such a vector (referred particularly to as a shuttle vector) that can transform both *Escherichia coli* and yeast. There are already several reports on shuttle vectors which can act in both *Escherichia coli* and *Saccharomyces cerevisiae* (a kind of yeast), such as $YE_p13$ [Broach, J. R., Strathern, N.J., Hicks, J. B., Gene, 8, 121, (1979)] and $YR_p7$ [Struhl, K., Stinchcomb, D. T., Scherer, S., Davis, R. W., Proc. Natl. Acad. Sci., 76, 1035 (1979)].

However, a shuttle vector capable of acting in a wider range of hosts is required. The present inventors paid attention to an autonomously replicating sequence (hereinafter referred to as ARS) from *Candida maltosa* which is a yeast but is different from *Saccharomyces cerevisiae* and by using the ARS they succeeded in construction of plasmids capable of becoming stable shuttle vectors not only in *Escherichia coli* and *Candida maltosa* but also in *Saccharomyces cerevisiae*.

SUMMARY OF THE INVENTION

According to the present invention, there are provided (1) plasmids containing an ARS of *Candida maltosa*, Leu 2 gene derived from *Saccharomyces cerecisiae* and an ampicillin resistance gene and (2) plasmids containing an ARS of *Candida maltosa*, Leu 2 gene derived from *Saccharomyces cerevisiae*, an ampicillin resistance gene and a tetracycline resistance gene.

According to the present invention, there is further provided a process for producing the plasmid described above in (1), which comprises the following steps (a) to (c).

Step (a): Using vector $YE_p13$ (containing Leu 2 gene) of *Saccharomyces cerevisiae*, a gene library of *Candida maltosa* is prepared.

Step (b): Then, using the above gene library, leucine-requiring *Candida maltosa* (a host) is transformed.

Step (c): A plasmid is recovered from the resulting transformant. Using the plasmid, *Escherichia coli* is transformed. An ampicillin resistance plasmid is recovered from the resulting transformant of *Escherichia coli*.

According to the present invention, there is further provided a process for producing plasmids claimed in this invention, which comprises the following steps (a) to (f).

Step (a): Using vector $YE_p13$ (containing Leu 2 gene) of *Saccharomyces cerevisiae*, a gene library of *Candida maltosa* is prepared.

Step (b): Then, using the above gene library, leucine-requiring *Candida maltosa* (a host) is transformed.

Step (c): A plasmid is recovered from the resulting transformant. Using the plasmid, *Escherichia coli* is transformed. An ampicillin resistance plasmid is recovered from the resulting transformant of *Escherichia coli*.

Step (d): The ampicillin resistance plasmid is cleaved with restriction enzyme BamHI to isolate a region (referred to as a TRA region) necessary for the transformation of *Candida maltosa*.

Step (e): Vector $YE_p13$ (containing Leu 2 gene) derived from *Saccharomyces cerevisiae* is cleaved with restriction enzyme BglII to isolate Leu 2 gene. Separately, vector pBR322 of *Escherichia coli* is cleaved with restriction enzyme EcoRI. The Leu 2 gene and the cleaved pBR322 are ligated.

Step (f): This pBR322 Leu 2 plasmid is cleaved with restriction enzyme XhoI and is ligated with the TRA region isolated in Step (d).

An ARS is defined as a DNA fragment which enables the autonomous propagation of a certain DNA fragment and of its own DNA fragment.

The plasmids (shuttle vectors) of the present invention can be utilized as follows. A useful foreign gene is inserted into a plasmid of the present invention; using the resulting new plasmid, *Escherichia coli* is transformed and cultured in order to obtain the plasmid in a large amount; and using this plasmid, *Saccharomyces cerevisiae* or *Candida maltosa* as a host is allowed to produce useful substances such as hormones and enzymes on a large scale. The useful foreign gene includes not only genes of animals and plants but also genes of bacteria such as yeasts (e.g. *Saccharomyces cerevisiae* and *Candida maltosa*) and *Escherichia coli*.

DETAILED DESCRIPTION OF THE INVENTION

Figure 1:
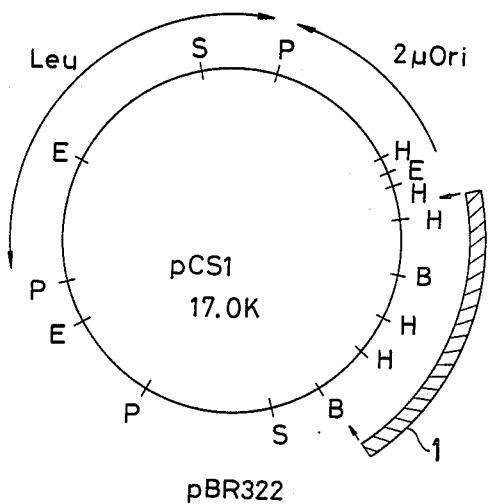
FIG. 1 shows the restriction map of pCSI, a plasmid of the present invention.

The novel plasmids of the present invention can be constructed as follows, for example.

Vector $YE_p13$ (containing Leu 2 gene) of *Saccharomyces cerevisiae* is cleaved with restriction enzyme BamHI. Into the cleavage site of $YE_p13$ is inserted a fragment obtained by subjecting the total DNA of *Candida maltosa* to partial cleavage with restriction enzyme Sau3AI. Using the resulting new plasmid, *Escherichia coli* is transformed and cultured. Ampicillin (Ap)-resistant and tetracycline (Tc)-sensitive colonies are isolated and a plasmid DNA is recovered therefrom. This plasmid is used as a gene library.

Using this gene library, leucine-requiring J288 strain of *Candida maltosa* (a host) is transformed in accordance with the protoplast method by Hinnen et al. [Hinnen, A., Hicks, J.B., Fink, G.R., *Proc. Natl. Acad. Sci.*, 75, 1929 (1978)] and then is allowed to propagate on a leucine-free minimal medium consisting of the following compositions.

Yeast nitrogen base w/o amino acid, manufactured by
  Difco CO.: 0.67%
  Glucose: 2%
  Sorbitol: 1.2M
  Agar: 2%

A plasmid DNA is recovered from the resulting transformants. Using this plasmid, *Escherichia coli* is transformed. Ap-resistant colonies are isolated and a novel plasmid (referred to as a pCSI) is recovered therefrom.

Next, pCSI is subjected to subcloning, namely, cleaved with restriction enzyme BamHI and there is separated TRA region which is a small region containing ARS necessary for transformation of *Candida maltosa*.

This TRA region is inserted into the BamHI cleavage site of vector YE$_p$13, whereby can be prepared a novel plasmid (referred to as pCS21) which is smaller than pCSI but has properties and functions similar to those of pCSI.

Like pCSI, the present plasmid pCS21 can transform both of *Candida maltosa* and *Saccharomyces cerevisiae*.

Vector YE$_p$13 (containing Leu 2 gene) of *Saccharomyces cerevisiae* is cleaved with restriction enzyme BglII to isolate Leu 2 gene. Separately, vector pBR322 of *Escherichia coli* [Bolivar, F., Rodrigulz, R. L., Greene, P. J., Belfach, M.C., Heynecker, H. L., Boyer, H. W., Gene, 2, 95 (1977)] is cleaved with restriction enzyme EcoRI. Leu 2 and the cleaved pBR322 are subjected to a ligation reaction to construct a new plasmid. This plasmid is cleaved with restriction enzyme XhoI and ligated with the TRA region mentioned above, whereby novel plasmids, namely, shuttle vectors (referred to as pTRAI and pTRAII) are constructed.

The reason why these two plasmids pTRAI and pTRAII are formed is that the TRA region is inserted into the plasmid obtained from Leu 2 and pBR322 in two opposite directions. Both of pTRAI and pTRAII are confirmed to function as an ARS in *Candida maltosa* and *Saccharomyces cerevisiae*.

EXAMPLES

Next the present invention will be described in more detail by way of Examples.

EXAMPLE 1

Construction of novel plasmid pCSI

Wild strain IAM12247 of *Candida maltosa* was cultured in YEPD medium containing 1% of yeast extract, 2% of peptone and 2% of glucose at 30° C. for 48 hours. A total DNA was extracted from the cells and subjected to partial cleavage by restriction enzyme Sau-3AI. Separately, vector YE$_p$13 (containing Leu 2) of *Saccharomyces cerevisiae* was cleaved with restriction enzyme BamHI. The resulting two DNAs were ligated with T4DNA ligation enzyme. Using this new DNA obtained from ligation, *Escherichia coli* was transformed. The transformed *Escherichia coli* was cultured for 12 hours in LB medium (1% of tryptone, 0.5% of yeast extract and 1% of NaCl, pH of 7.5) containing 50 μg/ml of Ap.

Among the resulting Ap-resistant colonies, 2,000 tetracycline (Tc) - sensitive colonies were obtained, from which a plasmid was recovered. This plasmid was used as a gene library of *Candida maltosa*.

Using this gene library, J288 strain (a leucine-requiring strain) of *Candida maltosa* as a host was transformed in accordance with the protoplast transformation method by Hinnen et al. and the transformed J288 strain was cultured in a leucine-free medium. The cells were grown at 30° C. for 4 to 5 days and the resulting colonies were isolated. These colonies were again cultured in a leucine-free liquid medium and a DNA was recovered from cells. Using this DNA, *Escherichia coli* was transformed and Ap-resistant colonies were isolated. A plasmid was recovered from the cells among the colonies. This plasmid was designated as pCSI.

EXAMPLE 2

Preparation of restriction map of pCSI

Plasmid pCSI was cleaved with restriction enzymes EcoRI, PstI, HindIII, BamHI and SalI. From the size of each fragment obtained, the relative position of each cleavage site was determined. The relative positions are shown in FIG. 1. Region 1 represents a DNA fragment (6.3 Kb) derived from *Candida maltosa*.

EXAMPLE 3

Preparation of restriction map of pCS21

Figure 2:
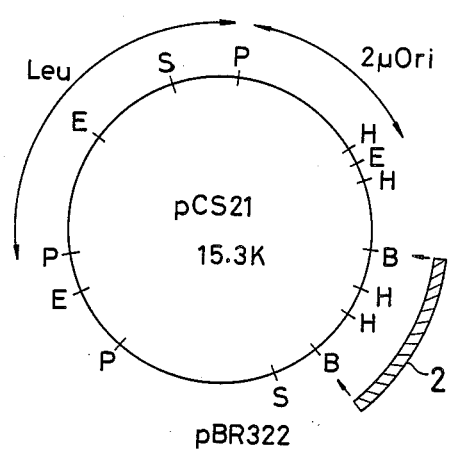
FIG. 2 shows the restriction map of pCS21, a plasmid of the present invention.

Plasmid pCS21 was cleaved with restriction enzymes EcoRI, PstI, HindIII, BamHI and SalI. From the size of each fragment obtained, the relative position of each cleavage site was determined. The relative positions are shown in FIG. 2. Region 2 represents a DNA fragment (TRA region of 3.4 Kb) derived from *Candida maltosa*.

EXAMPLE 4

Preparation of shuttle vectors pTRAI and pTRAII

Figure 3:
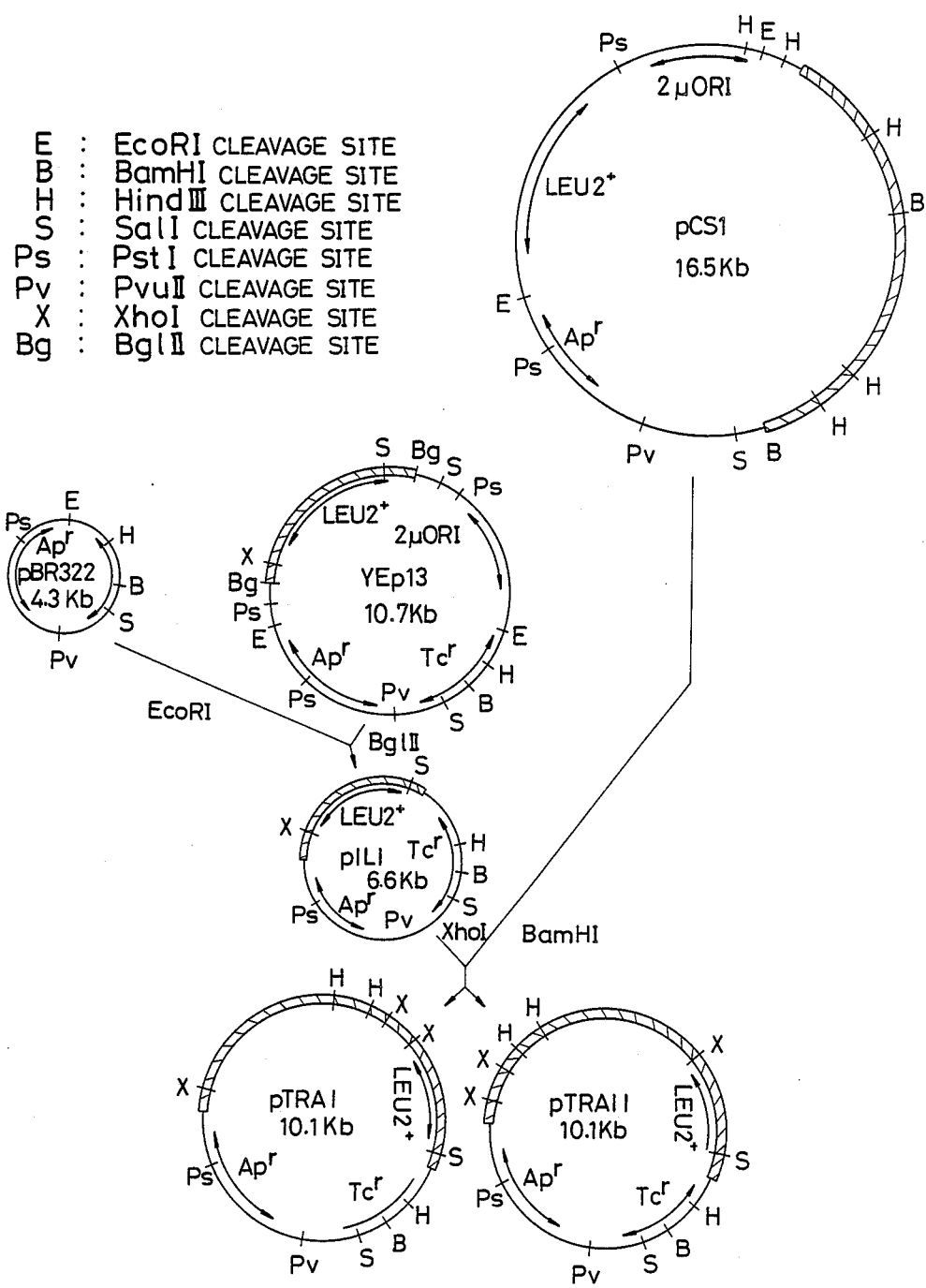
FIG. 3 shows the restriction map of pTRAI and pTRAII, each a plasmid of the present invention, as well as a process for constructing these plasmids.

A process for producing pTRAI and pTRAII will be described using a diagram of FIG. 3.

(1) Plasmid pCSI was cleaved with restriction enzyme BamHI and a fraction of 3.4 Kb (TRA region) was isolated. Both ends of the TRA region were made to flush ends using KLENOW fragment enzyme manufactured by Pharmacia Co., Sweden.

(2) Plasmid YEp13 was cleaved with restriction enzyme BglII and Leu 2 gene was isolated. Both ends of the gene were made to flush ends using KLENOW fragment enzyme.

(3) Vector pBR322 of *Escherichia coli* was cleaved with restriction enzyme EcoRI and both ends were made to flush ends with KLENOW fragment enzyme.

(4) Leu 2 gene obtained in (2) was ligated to the XhoI cleavage site of pBR322 obtained in (3) in accordance with a flush-end ligation reaction, whereby plasmid pILI was constructed.

(5) Plasmid pILI was cleaved with restriction enzyme XhoI and both ends were made to flush ends with KLENOW fragment enzyme. (6) TRA region obtained in (1) was ligated to the XhoI cleavage site of pILI obtained in (5) in accordance with a flush-end ligation reaction, whereby pTRAI and pTRAII having respective TRA region in opposite directions were constructed. *E. Coli* strain JA 221 transformed with pTRAI has been deposited under the terms of the Budapest Treaty at the Fermentation Research Institute, Japan and assigned accession number FERM BP-2346. Likewise, *E. coli* JA 221, transformed with pTRAII, has been deposited and accorded accession number FERM BP-2346.

Figure 4:
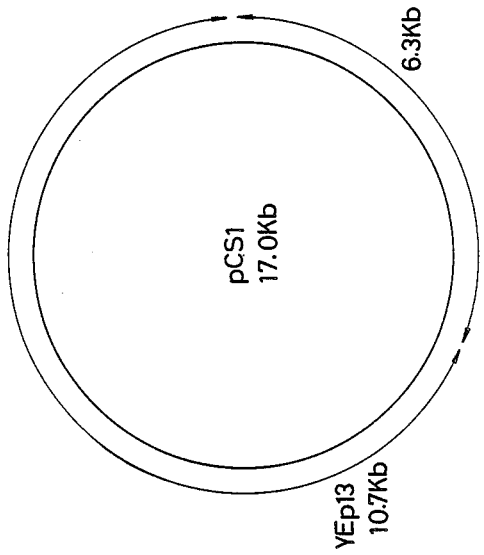
FIGS. 4 (a) and (b) show subcloning of TRA region obtained from plasmid pCSI, its restriction enzyme map, and leucine requirement of the transformants which are transfected with the plasmid containing corresponding subfragment.
Figure 4:
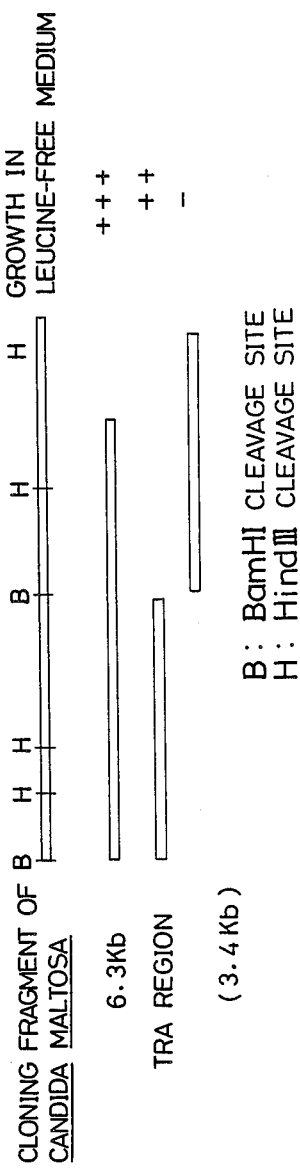

In FIGS. 4 (a) and (b) were shown subcloning of TRA region obtained from pCSI, its restriction enzyme map, and leucine-requirement of the transformants with respective plasmid containing subfragment.

EXAMPLE 5

Expression of plasmid pCSI and shuttle vectors pTRAI and pTRAII in *Candida maltosa* and *Saccharomyces cerevisiae*

There were used, as host microorganisms, *Candida maltosa* J288 strain (a leucine-requiring strain) and *Saccharomyces cerevisiae* AH22 strain (a leucine-requiring strain).

Method 1

Protoplast method by Hinnen et al.

Host cells were treated with Zymolyase to convert to protoplasts. Polyethylene glycol 4,000 and CaCl$_2$ were added to the protoplast suspension, and the mixture was embedded into a leucine-free agar medium containing 1.2M sorbitol and subjected to culture at 30° C. for 5 to 7 days. The number of the transformant strains formed per 1 μg of DNA is shown in a table given below.

Method 2

Lithium-metal method

In accordance with the lithium-metal method by Kimura et al., host cells were kept at 30° C. for 60 minutes in a solution containing 0.5 M LiCl, 35% of polyethylene glycol 6,000 and DNA and then seeded on a leucine-free agar medium. The efficiency of colony formation after culture at 30° C. for 4 to 5 days was examined. The number of the colonies formed per 1 μg of DNA is shown in the following table.

TABLE

| Plasmid | Protoplast method | | Lithium-metal method |
|---|---|---|---|
| | *Saccharomyces cerevisiae* | *Candida maltosa* | *Candida maltosa* |
| pCSI | 1,650 | 330 | 280 |
| pTRAI | 3,080 | 1,650 | 510 |
| pTRAII | 920 | 460 | 60 |

EXAMPLE 6

Expression of plasmid pCS21 in *Candida maltosa* and *Saccharomyces cerevisiae*

Using plasmid pCS21, *Candida maltosa* and *Saccharomyces cerevisiae* were transformed in accordance with the protoplast method by Hinnen et al., whereby 370 and 1,320 transformants per 1 μg of DNA were obtained, respectively. Also, *Candida maltosa* was transformed in accordance with the lithium-metal method by Kimura et al. [Ito H., Fukuda Y., Murata K., Kimura A., *J. Bacteriol.*, 153, 165 (1983)], whereby 60 transformants per 1 μg of DNA were obtained. These methods were found to be very useful for the expression of plasmid pCS21.

EXAMPLE 7

Stability of shuttle vectors pTRAI and pTRAII in *Candida maltosa* at propagation period The following experiment was carried out to examine the stability of pTRAI and pTRAII in the J288 strain of *Candida maltosa*. The transformant strain of *Candida maltosa* grown in a leucine-free medium was transferred into a full nutrient-liquid medium and cultured at 30° C. for 15 generations. Each sample was taken out at generation of culture shown in FIG. 5 and was placed in a full nutrient-agar medium for colony formation. The colonies formed were measured for its leucine requirement.

Figure 5:
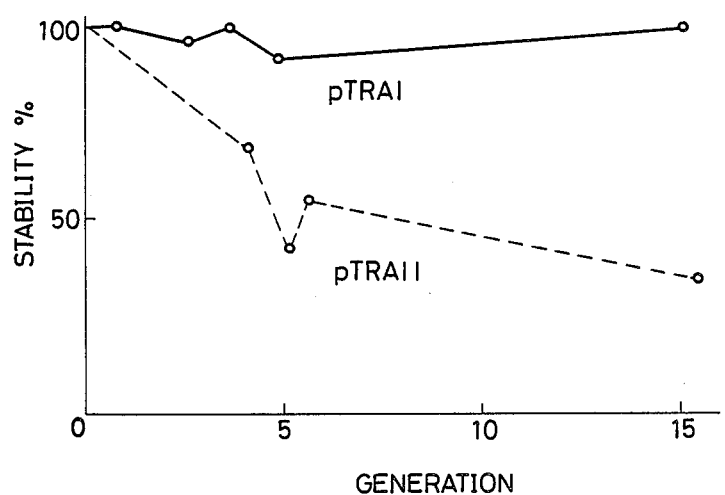
FIG. 5 is a graph showing the stabilities of pTRAI and pTRAII, plasmids of the present invention, in *Candida maltosa*.

As shown in FIG. 5, pTRAI and pTRAII were maintained stably in *Candida maltosa* J288 strain. The stability of pTRAI was particularly excellent.

As described above, the plasmids of the present invention can be utilized as shuttle vectors which are replicated and stably maintained not only in cells of *Escherichia coli* and *Candida maltosa* but also in cells of *Saccharomyces cerevisiae*.

What is claimed is:

1. A process for producing a plasmid comprising:
   (a) preparing a gene library of *C. maltosa* by partially digesting total *C. maltosa* DNA with Sau3AI and ligating the fragments into the BamHI restriction site of YEp13;
   (b) transforming *E. coli* cells with the plasmids prepared in step (a), isolating ampicillin resistant, tetracycline sensitive colonies therefrom, and recovering plasmid DNA from the isolated colonies;
   (c) transforming a leucine-dependent strain of *C. maltosa* with the plasmids recovered in step (b), growing said transformed cells in a leucine-free medium and isolating plasmid DNA from the surviving colonies;
   (d) transforming *E. coli* with the plasmid isolated in step (c), isolating ampicillin resistant colonies, and recovering the plasmid DNA therefrom;
   (e) digesting the plasmid recovered in step (d) with BamHI, and isolating the 3.4 Kb TRA region;
   (f) digesting plasmid YEp13 with Bgl II to isolate the Leu 2 gene and annealing the Leu 2 gene into the EcoRI site of pBR322; and
   (g) digesting the plasmid formed in step (f) with XhoI and annealing the DNA fragment obtained in step (e) into the XhoI restriction site.

2. A plasmid usable as a shuttle vector, produced by a process comprising:
   (a) preparing a gene library of *C. maltosa* by partially digesting total *C. maltosa* DNA with Sau3AI and ligating the fragments into the BamHI restriction site of YEp13;
   (b) transforming *E. coli* cells with the plasmids prepared in step (a), isolating ampicillin resistant, tetracycline sensitive colonies therefrom, and recovering plasmid DNA from the isolated colonies;
   (c) transforming a leucine-dependent strain of *C. maltosa* with the plasmids recovered in step (b), growing said transformed cells in a leucine-free medium and isolating plasmid DNA from the surviving colonies;
   (d) transforming *E. coli* with the plasmid isolated in step (c), isolating ampicillin resistant colonies, and recovering the plasmid DNA therefrom;
   (e) digesting the plasmid recovered in step (d) with BamHI, and isolating the 3.4 kb TRA region;
   (f) digesting plasmid YEp13 with Bgl II to isolate the Leu 2 gene and annealing the Leu 2 gene into the Eco RI site of pBR322;
   (g) digesting the plasmid formed in step (f) with XhoI and annealing the DNA fragment obtained in step (e) into the XhoI restriction site.

3. A plasmid usable as a shuttle vector consisting essentially of an autonomously replicating sequence of *Candida maltosa,* a Leu 2 gene derived from *Saccharomyces cerevisiae,* an ampicillin resistance gene and a tetracycline resistance gene, wherein said autonomous replicating sequence of *Candida maltosa* is inserted between said Leu 2 gene and said ampicillin resistance gene, said plasmid being stably maintained in *Escherichia coli, Candida maltosa* and *Saccharomyces cerevisiae* and designated pTRA I.

4. A plasmid usable as a shuttle vector consisting essentially of an autonomously replicating sequence of *Candida maltosa,* a Leu 2 gene derived from *Saccharomyces cerevisiae,* an ampicillin resistance gene and a tetracycline resistance gene, wherein said autonomous replicating sequence of *Candida maltosa* is inserted between said Leu 2 gene and said ampicillin resistance gene, said plasmid being stably maintained in *Escherichia coli, Candida maltosa* and *Saccharomyces cerevisiae* and designated pTRA II.

* * * * *